US008871502B2

(12) United States Patent
Liu et al.

(10) Patent No.: US 8,871,502 B2
(45) Date of Patent: Oct. 28, 2014

(54) CULTURE MEDIUM DEVICE

(71) Applicant: Balay Biotechnology Corporation, Hsinchu (TW)

(72) Inventors: Wen-Huang Liu, Hsinchu County (TW); Chien-Liang Kuo, Changhua County (TW)

(73) Assignee: Balay Biotechnology Corporation, Hsinchu (TW)

( * ) Notice: Subject to any disclaimer, the term of this patent is extended or adjusted under 35 U.S.C. 154(b) by 0 days.

(21) Appl. No.: 13/749,868

(22) Filed: Jan. 25, 2013

(65) Prior Publication Data

US 2014/0178981 A1 Jun. 26, 2014

(30) Foreign Application Priority Data

Dec. 26, 2012 (TW) .............................. 101149017 A

(51) Int. Cl.
*C12M 1/22* (2006.01)
*C12M 1/12* (2006.01)

(52) U.S. Cl.
CPC ............... *C12M 25/06* (2013.01); *C12M 23/10* (2013.01)
USPC ..................................... 435/305.4; 435/305.1

(58) Field of Classification Search
CPC ..... B01L 3/5085; C12M 27/20; C12M 1/123; C12M 23/10; C12M 25/06; C07K 14/705; C12N 9/78; C12N 9/0065; C12N 15/82; C12N 1/22; C12Q 1/28; A01H 4/005; A61K 31/715; A01N 25/28

USPC ........... 435/283.1, 289.1, 303.1, 305.1, 305.4
See application file for complete search history.

(56) References Cited

U.S. PATENT DOCUMENTS

| 4,466,216 A * | 8/1984 | Howard .......................... 435/425 |
| 5,166,068 A * | 11/1992 | Fujimura et al. ............... 435/421 |
| 2002/0092037 A1 * | 7/2002 | Connett-Porceddu et al. .............................. 435/422 |
| 2008/0064090 A1 * | 3/2008 | Whittlinger ................ 435/305.3 |
| 2008/0140036 A1 * | 6/2008 | Buck et al. ..................... 424/404 |
| 2010/0297696 A1 * | 11/2010 | Chotani et al. ................ 435/183 |

* cited by examiner

*Primary Examiner* — Michael Marcheschi
*Assistant Examiner* — Timothy Barlow
(74) *Attorney, Agent, or Firm* — Rosenberg, Klein & Lee

(57) ABSTRACT

The present invention discloses a culture medium device, which comprises a plate containing a solid-state or gel-state culture medium layer; a shield layer covering the culture medium layer; and a lid covering the plate. The shield layer is in a solid, gel or liquid state and contains sugar at a concentration of greater than 0% (w/w) and less than or equal to 0.1% (w/w). Via the shield layer containing a select composition, the present invention can reduce the affection of microbiological contamination and promote the yield and productivity of biomass in the process of inoculating and cultivating Polyporales.

8 Claims, 2 Drawing Sheets

CULTURE MEDIUM DEVICE

BACKGROUND OF THE INVENTION

1. Field of the Invention

The present invention relates to a culture medium device, particularly to a culture medium device for cultivating Polyporales to generate the biomass thereof.

2. Description of the Related Art

Polyporales are generally called mushrooms, categorized into the system of Fungi, Basidiomycota, Agaricomycotina, Agaricomycetes, Agaricomycetidae in the biological classification system. Mushrooms were all gathered from the wild before. Nowadays, they are normally cultured artificially, or even mass-cultivated commercially because of their deliciousness and nutrition. Polyporales are also used in healthcare foods or medicine development. Therefore, Polyporales culture has been an emerging subject in the field concerned.

In order to promote productivity, the production of the biomass of fungi is usually realized via submerged culture and solid-state fermentation, wherein microorganisms are cultivated in a culture medium with a given composition under an environment of appropriate acidity, temperature and ventilation.

Refer to FIG. 1 showing a conventional culture medium device for generating biomass of fungi. The conventional culture device comprises a plate 10, a culture medium 12 contained in the plate 10, and a lid 14 covering the plate 10 and having a gap between itself and the plate 10 for ventilation. The conventional culture system is normally equipped with devices for maintaining appropriate temperature, humidity, airflow, oxygen content and carbon dioxide content, which are likely to cause aerosol carried by airflow to pass through the gap, which is formed between the lid 14 and the plate 10 for aerobic culture, and deposit on the surface of the culture medium. Such a culture system may cause the culture medium to be contaminated by heterogeneous population in batch production and thus has a lower yield. A clean room can reduce the damage caused by heterogeneous populations. However, the clean room would greatly increase the cost.

Accordingly, the present invention proposes a culture medium device to overcome the abovementioned problems.

SUMMARY OF THE INVENTION

The primary objective of the present invention is to provide a culture medium device, wherein the shield layer over the culture medium layer can reduce the affection of heterogeneous population contamination, decrease the growth rate of heterogeneous populations, and promote the yield and productivity of biomass of Polyporales in the process of from cultivating Polyporales to harvesting the biomass thereof.

To achieve the abovementioned objective, the present invention proposes a culture medium device, which comprises a plate containing a culture medium layer; a shield layer arranged inside the plate, covering the surface of the culture medium layer, and containing sugar at a concentration of x, wherein $0 < x \leq 0.1\%$; and a lid covering the plate, wherein a ventilation gap exists between the lid and the plate. Thereby, the present invention can realize the abovementioned objective via the shield layer.

The culture medium layer contained in the plate is a solid-state culture medium or a gel-state culture medium. The shield layer is an agar layer, an inorganic agar layer, a glycerol layer, a vegetable oil layer, or a layer containing a plant essential oil at a concentration of 0.001 mg/mL-10 mg/mL.

Below, embodiments are described in detail in cooperation with the attached drawings to make easily understood the objectives, technical contents, characteristics and accomplishments of the present invention.

DETAILED DESCRIPTION OF THE INVENTION

The present invention provides a culture medium device, which can reduce the microbiological contamination, which is designed to have a shield layer possessing select components and formed on the surface of the culture medium layer. The shield layer possessing select components can reduce the affection of microbiological contamination during the course from cultivating Polyporales to harvesting the biomass thereof. Thus is decreased the damage caused by microbiological contamination.

Figure 1:
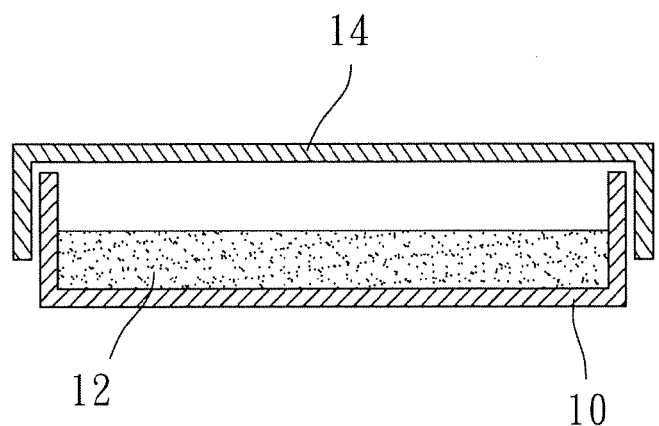
FIG. 1 is a diagram schematically showing a conventional culture medium device.
Figure 2:
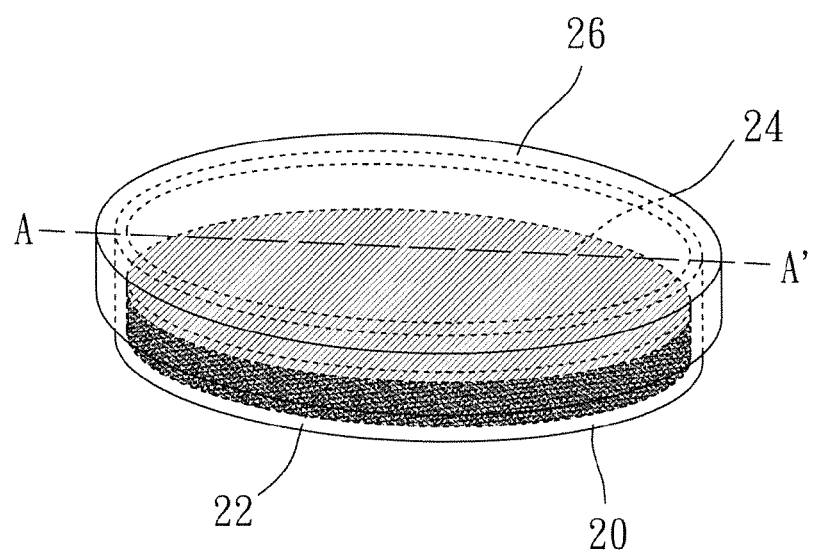
FIG. 2 is a perspective view schematically showing a culture medium device according to one embodiment of the present invention.
Figure 3:
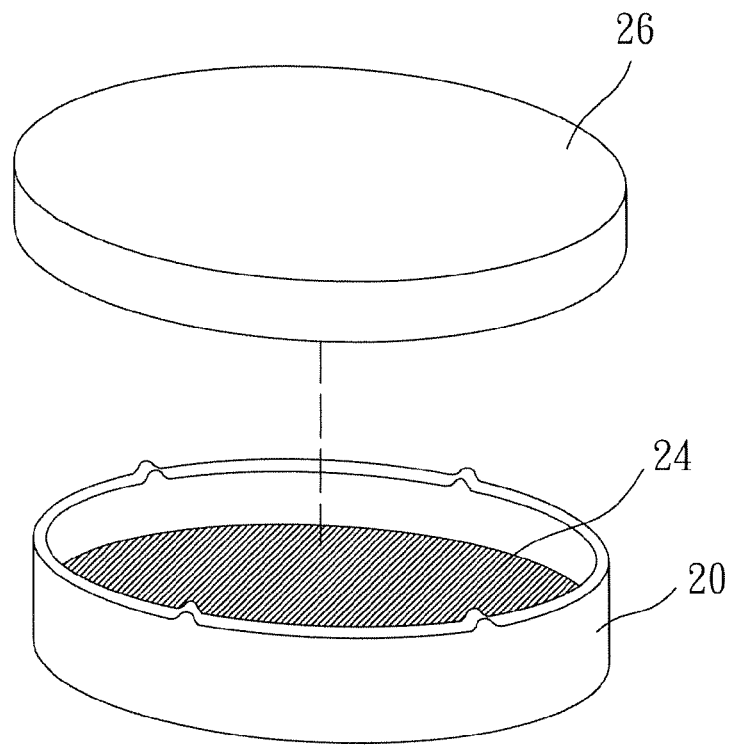
FIG. 3 is an exploded view schematically showing a culture medium device according to one embodiment of the present invention.
Figure 4:
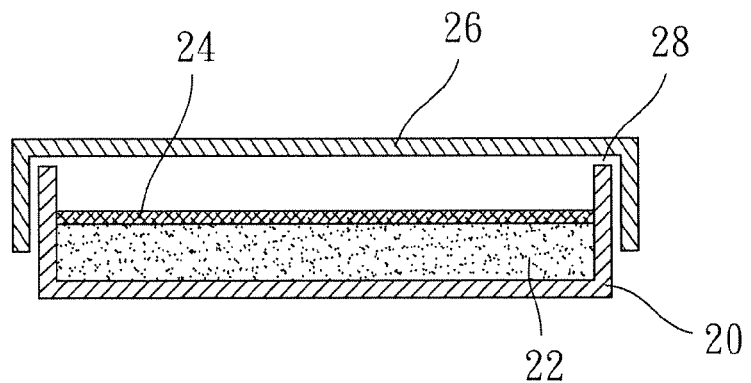
FIG. 4 is a sectional view schematically showing a culture medium device according to one embodiment of the present invention.

Refer to FIGS. 2-4 respectively a perspective view, an exploded view and a sectional view of a culture medium device according to one embodiment of the present invention. The culture medium device of the present invention comprises a plate 20, a culture medium layer 22, a shield layer 24 and a lid 26. The culture medium layer 22 is contained by the plate 20 and has a solid-state culture medium or a gel-state culture medium. The shield layer 24 is in a solid state, a gel state, or a liquid state. The shield layer 24 is formed on the culture medium layer 22 via smearing, picking and placing, spraying, pouring, dripping, coating, or condensing. The shield layer 24 contains sugar at a concentration of x, and $0 < x \leq 0.1\%$. The shield layer 24 has a thickness of 1 μm-1 cm. In one embodiment, the shield layer 24 is an agar layer, an inorganic agar layer, an organic layer, a glycerol layer, a vegetable oil layer, or a layer containing a plant essential oil at a concentration of 0.001 mg/mL-10 mg/mL In other words, the shield layer 24 contains sugar at a concentration of greater than 0% (w/w) and less than or equal to 0.1% (w/w), and the residual of the shield layer 24 is agar, inorganic agar, an organic material, glycerol, vegetable oil, a solution containing plant essential oil, or the combination thereof. The lid 26 covers the plate 20, and a gap 28 exists between the lid 26 and the plate 20.

The selected components of the shield layer are firstly treated with a sterilization process to guarantee that the shield layer is free of microbiological contamination. The sterilization process is realized with a high-temperature sterilization method, a high-temperature and high-pressure sterilization method, an ultraviolet sterilization, a filtering sterilization method, a fumigation method, or a gamma-ray method.

For the shield layer 24 containing the selected components, the agar layer contains 0.1%-5% agar; the inorganic agar layer contains at least one inorganic additive selected from a group consisting of $MgSO_4$, $NH_4H_2PO_4$, $K_2HPO_4$, NaCl, $MgCl_2$, $CaSO_4$, $NaHCO_3$, $KFe(SO_4)_2 \cdot 12H_2O$ and $K_3[Fe(CN)_6]$, and the additive has a concentration of less than or equal to 0.1% (w/w); the vegetable oil contains at least one oil selected from a group consisting of olive oil, clove oil, lemon oil, mustard oil, Canola oil, sesame oil, and flax-seed oil. The plant essential oil contains at least one essential oil selected from a group consisting of essential oils of *Sardinian thymus*, *Litsea cubeba*, *Farges fir*, *Cirmamonuun cainophor*, Cypress, *Shaddock pericarp*, *Cinnamomum kanehirae*, *Artemisiae argyi*, camphor, *Melaleuca alternifolia*, *Thymus vulgaris*, *Rosmarinus officinalis*, *Syzygium aromaticum*, *Origanum vulgare*, *Origanum vulgare*, *Cuminum cyminum L.*, *Salvia sclarea*, *Pogostemon cablin*, *Asarum*, Lemon grass, Rosemary, *Crossostephium chinense*, *Eucalyptus camaldulensis* leaves, *Hiba Falsearborvitae* leaves, Chinese fir wood, Taiwan cypress heartwood, Taiwan red cypress, *Taiwania cryptomerioides* heartwood, and Taiwan incense cedar heartwood.

Below is described the process of using the culture medium device to cultivate Polyporales and generate the biomass thereof. The process includes steps: (1) preparing a culture medium; (2) treating the culture medium with a sterilization process; (3) forming a culture medium layer on a plate; (4) preparing select components for a shield layer; (5) treating the select components with a sterilization process; (6) spreading the select components on the surface of the culture medium to function as a shield layer; (7) inoculating the strain of Polyporales on the shield layer; and (8) cultivating the culture medium device containing the strain of Polyporales in a special environment for a given interval of time to generate a great amount of biomass.

Below, several experiments are used to prove that the present invention can indeed promote the yield.

In a first experiment, pour a nutrient media, i.e. MEA (Malt Extract Agar), on the bottoms of sterilized plastic culture plate (having a diameter of 9 cm) to function as a culture medium layer. Next, overlay the nutrient media of the culture medium device of the present invention with a shield layer, which has 3.0% (w/v) agar and a thickness of 1.0±0.3 mm and is free of other carbon sources and nitrogen sources. The strain of *Ganoderma lucidum* is used in the first experiment. Next, perform inoculation in a sterile bench. Next, place the culture medium devices containing the strain of of *Ganoderma lucidum* in a thermostatic incubator at a temperature of 28±1° C. and with airflow circulation for 28 days. Next, use naked eyes to examine each of 50 plates to count the numbers of CFUs (Colony Forming Units) of bacteria and fungi and the diameters of colonies of bacteria and fungi. Table. 1 and Table. 2 respectively list the statistics of the CFU numbers and the colony diameters of bacteria and fungi in different culture medium devices. In the present invention, the shield layer is made of low-nutrition materials. Thus, the spores of bacteria and heterogeneous populations are harder to grow in the culture medium device of the present invention, as shown in Table. 1 and Table. 2. Therefore, the culture medium device of the present invention can achieve a higher yield.

TABLE 1

| Cultivation method | CFU number/each plate | |
|---|---|---|
| | Bacteria (CFU) | Fungi (CFU) |
| MEA | 8.51 ± 1.67 | 13.25 ± 5.03 |
| The present invention: Upper layer: 3.0% (w/v) agar Lower layer: MEA | 2.25 ± 1.41 | 2.80 ± 2.08 |

TABLE 2

| Cultivation method | Colony diameter | |
|---|---|---|
| | Bacteria (mm) | Fungi (mm) |
| MEA | 5.55 ± 0.89 | 22.40 ± 4.28 |
| The present invention: Upper layer: 3.0% (w/v) agar Lower layer: MEA | 1.55 ± 0.46 | 5.95 ± 2.42 |

In a second experiment, pour a nutrient media, i.e. PDA (Potato Dextrose Agar), on the bottoms of sterilized plastic culture plate (having a diameter of 9 cm) to function as a culture medium layer. Next, overlay the nutrient media of the culture medium device of the present invention with a shield layer, which has 0.8% (w/v) agar and 0.25% sodium chloride, and which has a thickness of 1.0±0.3 mm. The strain of *Phellinus linteus* is used in the second experiment. Next, perform inoculation in a sterile bench. Next, place the culture medium devices containing the strain of *Phellinus linteus* in a thermostatic incubator at a temperature of 25±1° C. and with airflow circulation for 28 days. Next, use naked eyes to examine each of 250 culture plates to count the ratios of the culture plates contaminated by bacteria or fungi and the yields and list the results in Table. 3. From Table. 3, it is learned that the culture medium device of the present invention can promote the yield by 11.2%. Therefore, the experiment proves that the shield layer of the present invention, which contains select low-nutrition components, can make the spores of bacteria and heterogeneous populations harder to grow and achieve a higher yield.

TABLE 3

| Cultivation method | Index | |
|---|---|---|
| | Count of plate not contaminated by bacteria or fungi | Yield (%) |
| PDA | 204 | 81.6% |
| The present invention: Upper layer: 0.8% (w/v) agar layer with 0.25% sodium chloride Lower layer: PDA nutrient layer | 232 | 92.8% |

In a third experiment, pour a nutrient media, i.e. MEA, on the bottoms of sterilized plastic culture plate (having a diameter of 9 cm) to function as a culture medium layer. Next, overlay the nutrient media of the culture medium device of the present invention with a shield layer, which has 0.12% essential oil of Chinese fir wood and is free of other carbon sources and nitrogen sources, and which has a thickness of 5-100 μm. The strain of *Gannoderma lucidum* is used in the third experiment. Next, perform inoculation in a sterile bench. Next, place the culture medium devices containing the strain of *Gannoderma lucidum* in a thermostatic incubator at a temperature of 25±1° C. and with airflow circulation for 28 days. Next, use naked eyes to examine each of 50 culture plates to count the numbers of CFUs of bacteria and fungi and the diameters of colonies of bacteria and fungi. Table. 4 lists the statistics of the CFU numbers and the colony diameters of bacteria and fungi in different culture medium devices. Because of adopting a low-nutrition shield layer, the culture medium device of the present invention can make the spores of bacteria and heterogeneous populations harder to grow and achieve a higher yield.

TABLE 4

| Cultivation method | CFU number/each plate | |
|---|---|---|
| | Bacteria (CFU) | Fungi (CFU) |
| MEA | 9.47 ± 1.24 | 15.13 ± 4.28 |
| The present invention: overlaying MEA with a shield layer containing 0.12% essential oil of Chinese fir wood | 3.17 ± 1.25 | 3.43 ± 1.19 |

In the conventional technology, the culture medium device is used to artificially cultivate Polyporales, cooperating with the control systems of temperature, humidity, airflow, oxygen and carbon dioxide. However, the heterogeneous populations would be carried by the airflow of the control systems, passing through the ventilation gap between the lid and the plate and depositing on the surface of the culture medium. The present invention overcomes the abovementioned problem via overlaying the culture medium layer with a shield layer containing a select composition, reducing the growth rate of heterogeneous populations, effectively increasing the yield of Polyporales and promoting the productivity of biomass.

The embodiments described above are to demonstrate the technical thought and characteristics of the present invention to enable the persons skilled in the art to understand, make, and use the present invention. However, they are not intended to limit the scope of the present invention. Any equivalent modification or variation according to the spirit of the present invention is to be also included within the scope of the present invention.

What is claimed is:

1. A culture medium device comprising:
   a plate containing a culture medium layer, said culture medium layer is made of a solid-state culture medium or a gel-state culture medium;
   a shield layer arranged inside said plate, covering an upper surface of said culture medium layer, and containing sugar at a concentration of x, wherein 0<x<0.1%(w/w), said shield layer being an agar layer with a thickness of 1.0 ±0.3 mm, an inorganic agar layer including inorganic additives with a thickness of 1.0 ±0.3 mm, or a layer containing a plant essential oil, the plant essential oil being at a concentration of 0.001 mg/mL-10 mg/mL and with a thickness of 5 μm-100 μm; and
   a lid covering said plate, wherein a ventilation gap exists between said lid and said plate.

2. The culture medium device according to claim 1, wherein said agar layers contain 0.1%-5% of agar.

3. The culture medium device according to claim 1, wherein said inorganic agar layer contains at least one inorganic additive selected from a group consisting of $MgSO_4$, $NH_4H_2PO_4$, $K_2HPO_4$, NaCl, $MgCl_2$, $CaSO_4$, $NaHCO_3$, $KFe(SO_4)_2 \cdot 12H_2O$ and $K_3[Fe(CN)_6]$.

4. The culture medium device according to claim 1, wherein said plant essential oil contains at least one essential oil selected from a group consisting of essential oils of *Sardinian thymus, Litsea cubeba, Farges fir, Cirmamonuun cainophor*, Cypress, *Shaddock pericarp, Cinnamomum kanehirae, Artemisiae argyi*, camphor, *Melaleuca alternifolia, Thymus vulgaris, Rosmarinus officinalis, Syzygium aromaticum, Origanum vulgare, Origanum vulgare, Cuminum cyminum L., Salvia sclarea, Pogostemon cablin, Asarum*, Lemon grass, Rosemary, *Crossostephium chinense, Eucalyptus camaldulensis* leaves, *Hiba falsearborvitae* leaves, Chinese fir wood, Taiwan cypress heartwood, Taiwan red cypress, *Taiwania cryptomerioides* heartwood, and Taiwan incense cedar heartwood.

5. The culture medium device according to claim 1, wherein said shield layer is in a solid state, a gel state, or a liquid state.

6. The culture medium device according to claim 1, wherein said shield layer has a select composition comprising selected sterilized components treated with a sterilization process.

7. The culture medium device according to claim 6, wherein said sterilization process includes at least one of a temperature sterilization method, a temperature and pressure sterilization method, an ultraviolet sterilization, a filtering sterilization method, a fumigation method, or a gamma-ray method.

8. The culture medium device according to claim 1, wherein said shield layer is formed on an upper surface of said culture medium layer via smearing, picking and placing, spraying, pouring, dripping, coating, or condensing.

* * * * *